(12) United States Patent
Jung et al.

(10) Patent No.: US 9,687,430 B2
(45) Date of Patent: Jun. 27, 2017

(54) COSMETIC KIT COMPRISING EFFERVESCENT TABLET AND SKIN TONER

(71) Applicant: AMOREPACIFIC CORPORATION, Seoul (KR)

(72) Inventors: Ju A Jung, Yongin-si (KR); Byung Ryol Paik, Yongin-si (KR); Chang Keun Lee, Yongin-si (KR); Lee Kyoung Kwon, Yongin-si (KR); Joon Ho Bae, Yongin-si (KR); Young So Kim, Yongin-si (KR)

(73) Assignee: AMOREPACIFIC CORPORATION, Seoul (KR)

( * ) Notice: Subject to any disclaimer, the term of this patent is extended or adjusted under 35 U.S.C. 154(b) by 0 days.

(21) Appl. No.: 14/892,081

(22) PCT Filed: Mar. 21, 2014

(86) PCT No.: PCT/KR2014/002392
§ 371 (c)(1),
(2) Date: Nov. 18, 2015

(87) PCT Pub. No.: WO2014/193076
PCT Pub. Date: Dec. 4, 2014

(65) Prior Publication Data
US 2016/0106646 A1 Apr. 21, 2016

(30) Foreign Application Priority Data
May 30, 2013 (KR) ................ 10-2013-0061761

(51) Int. Cl.
*A61Q 19/02* (2006.01)
*A61K 8/365* (2006.01)
*A61Q 19/00* (2006.01)
*A61K 8/02* (2006.01)
*A61K 8/06* (2006.01)
*A61K 8/19* (2006.01)

(52) U.S. Cl.
CPC .............. *A61K 8/365* (2013.01); *A61K 8/022* (2013.01); *A61K 8/06* (2013.01); *A61K 8/19* (2013.01); *A61Q 19/00* (2013.01); *A61Q 19/007* (2013.01); *A61Q 19/02* (2013.01); *A61K 2800/222* (2013.01); *A61K 2800/882* (2013.01)

(58) Field of Classification Search
CPC ...... A61Q 19/00; A61Q 19/007; A61K 8/365; A61K 2800/882
USPC ............................................. 424/44
See application file for complete search history.

(56) References Cited

U.S. PATENT DOCUMENTS 6,143,307 A   11/2000  Maurin
6,197,338 B1  3/2001   Nurnberg et al.

FOREIGN PATENT DOCUMENTS

| KR | 100264418 B1 | 8/2000 |
| KR | 1020080037857 A | 5/2008 |
| KR | 1020100082750 A | 7/2010 |
| WO | 2004/000261 | * 12/2003 |
| WO | 2004000261 A1 | 12/2003 |

OTHER PUBLICATIONS

Aldrich, title: surfactant classification by HLB numbers; downloaded from http://www.sigmaaldrich.com/material sciece on Jul. 29, 2016.*
Lotioncrafter, title: Dipropylene Glycol; downloaded from http://www.lotioncrafter.com/dipropylene-glycol-dpg.html on Nov. 23, 2016.*
International Search Report with English Translation for International Application No. PCT/KR2014/002392 dated Jul. 17, 2014.
Written Opinion for International Application No. PCT/KR2014/002392 dated Jul. 17, 2014.

* cited by examiner

*Primary Examiner* — Yanzhi Zhang
(74) *Attorney, Agent, or Firm* — Cantor Colburn LLP

(57) ABSTRACT

One aspect of the present invention relates to an effervescent tablet comprising a water-soluble lubricating agent, and a carbonated water cosmetic composition enabled to be used together therewith. One aspect of the present invention relates to an effervescent tablet comprising a crystalline #-hydroxy acid and a water-soluble lubricating agent, and a cosmetic composition using a skin toner for preventing the tablet from floating and allowing the tablet to rapidly form carbon dioxide gas in the cosmetic composition so as to maximize the visual effect and also the effect of carbon dioxide, thereby showing skin whitening, brightening and moisturizing effects and improving the pores.

4 Claims, No Drawings

COSMETIC KIT COMPRISING EFFERVESCENT TABLET AND SKIN TONER

TECHNICAL FIELD

The following disclosure relates to a cosmetic kit including a bubbling tablet and skin water. The following disclosure also relates to skin water including carbonated water.

BACKGROUND ART

Bubbling tablets are used frequently in pharmaceutical dosage forms, such as gastro retentive tablets, which float at the upper part of gastric juice and discharge drug continuously. A buoyancy system is a form designed in such a manner that it floats at the top of gastric juice in the stomach by incorporating a bubble (frequently, $CO_2$)-generating ingredient (carbonate, bicarbonate salts) additionally to a form containing drug to reduce the density of form by the bubbles thus generated. The reaction is generally based on the following reaction:

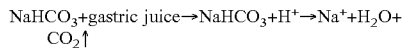

In addition, bubbling tablets facilitate stabilization of vitamin C and are used frequently in the food industry as vitamin C bubbling tables dropped and dissolved in water for drinking.

DISCLOSURE

Technical Problem

In the case of skin water, it includes a moisturizer, softener, solubilizer, solvent, fragrance or the like in addition to water so that a bubbling tablet may float in a composition or undergo slow bubbling, and has a limitation in its size in view of the size of an ejection portion of container. In addition, since a cosmetic composition should be used not for a short time but for a long time, it is required for a bubbling tablet to be dissolved completely in the composition with no precipitation. Particularly, when carbonic acid bubbles at the surface, it is difficult to realize visually a carbonic acid bubbling effect to be sought by the form of a bubbling tablet. In addition, due to the volatility of carbonic acid, the amount of carbonic acid evaporated to the air becomes larger than the amount of carbonic acid dissolved in skin water. Therefore, it is difficult to deliver a skin cosmetic effect given by carbonic acid.

Technical Solution

In one general aspect, there is provided a cosmetic kit including a bubbling tablet and skin water. In another general aspect, there is provided a bubbling tablet including sodium bicarbonate, alpha-hydroxyl acid, crystalline alpha-hydroxyl acid and a water-soluble lubricant. In still another aspect, there is provided skin water including an aliphatic compound having a hydroxyl group (—OH), emollient, surfactant and carbonated water. In still another aspect, there is provided a bubbling tablet including sodium bicarbonate, alpha-hydroxyl acid, crystalline alpha-hydroxyl acid and a water-soluble lubricant in a weight ratio of 3.0-70.0:1.0-70.0:1.0-70.0:1.0-5.0 (sodium bicarbonate:alpha-hydroxyl acid:crystalline alpha-hydroxyl acid:a water-soluble lubricant). In yet another aspect, there is provided skin water including an aliphatic compound having a hydroxyl group (—OH), emollient, surfactant and carbonated water in a ratio of 0-99.0:0-99.0:0.001-5.0:0.01-99.0.

Advantageous Effects

According to an embodiment of the present invention, a bubbling tablet has an optimized specific gravity and surface tension, and thus can show a delay in floating while maintaining high bubbling capability in skin water. In addition, according to an embodiment, it is possible to incorporate at least a predetermined amount of carbonated water to skin water, as well as to increase the concentration of carbonic acid in skin water during the bubbling of a bubbling tablet. As a result, according to an embodiment of the present invention, on one hand, carbonic acid bubbles contained in skin water increase the oxygen saturation degree in capillaries and improve the blood circulation, thereby improving the complexion. According to an embodiment of the present invention, on the other hand, skin barriers are reinforced, differentiation of dead skin cells are facilitated so that old dead skin cells are exfoliated with ease and a healthy corneum is maintained, thereby providing skin whitening, brightening and moisturizing effects. Further, according to an embodiment of the present invention, skin barriers are reinforced, the elasticity around pores is increased and pore shades are removed to provide skin with brightening and pore-care effects.

BEST MODE

The cosmetic kit disclosed herein may include a bubbling tablet and/or skin water.

According to an embodiment of the present invention, the bubbling tablet may include sodium bicarbonate; alpha-hydroxyl acid; crystalline alpha-hydroxyl acid; or a water-soluble lubricant. According to another embodiment, the bubbling tablet may include sodium bicarbonate in an amount of 3.0-70.0 wt %, particularly 10.0-40.0 wt %, based on the total weight of a composition of the bubbling tablet. According to still another embodiment, the bubbling tablet may include the alpha-hydroxyl acid in an amount of 1.0-70.0 wt %, particularly 5.0-20.0 wt %, based on the total weight of the composition. According to still another embodiment, the bubbling tablet may include the crystalline alpha-hydroxyl acid in an amount of 1.0-70.0 wt %, particularly 1.0-10.0 wt %, based on the total weight of the composition. According to yet another embodiment, the bubbling tablet may include the water-soluble lubricant in an amount of 1.0-10.0 wt %, particularly 1.0-5.0 wt %, based on the total weight of the composition.

Bubbling tablets are used in the field of cosmetics to stabilize water-soluble active ingredients, including vitamin C (ascorbic acid), kojic acid, albutin, niacinamide, acetyl glucosamine and minerals, and to provide the skin with such useful ingredients in a visually favorable and fresh manner.

As used herein, the crystalline alpha-hydroxyl acid may be hydrated or anhydrous crystalline alpha-hydroxyl acid. According to an embodiment, the crystalline alpha-hydroxyl acid may be citric acid and/or adipic acid. According to another embodiment, the water-soluble lubricant may be polyethylene glycol 4000 or polyethylene glycol 6000. The water-soluble lubricant serves as lubricant for a molding punch and enhances the flowability of a mixture. According to still another embodiment, the bubbling tablet may further include a binder for carrying out molding into the form of a tablet, and the binder may be polyvinyl pyrrolidone (PVP). In this case, according to an embodiment, the binder may be used in an amount of 0.5-5.0 wt %, particularly 0.5-3.0 wt %, based on the total weight of the composition. According to yet another embodiment, the bubbling tablet may further include an excipient for carrying out molding into the form of a tablet. According to an embodiment, the excipient may be a filler, such as mannitol or lactose. In this case, according to an embodiment, the excipient may be used in an amount (wt %) of 100 wt % minus the combined weight percent of the other ingredients forming the bubbling tablet.

According to an embodiment, the skin water may include at least one selected from the group consisting of an aliphatic compound having a hydroxyl group (—OH), emollient, surfactant and carbonated water. According to an embodiment, the skin water may include the aliphatic compound having a hydroxyl group (—OH) in an amount of 0-99.0 wt % based on the total weight of the skin water. The skin water may include the emollient in an amount of 0-99.0 wt % based on the total weight of the skin water. The skin water may include the surfactant in an amount of 0.001-5.0 wt % based on the total weight of the skin water. The skin water may include the carbonated water in an amount of 0.01-99.0 wt % based on the total weight of the skin water.

According to an embodiment, the aliphatic compound having a hydroxyl group (—OH) may be at least one selected from the group consisting of ethanol and glycerin which is polyhydric alcohols, butylene glycol, propylene glycol, hexylene glycol, propanediol, dipropylene glycol, etc. According to another embodiment, 1.0-10.0 wt % of ethanol may be used based on the total weight of the skin water. According to still another embodiment, 0-15.0 wt % of butylene glycol may be used based on the total weight of the skin water. According to yet another embodiment, a mixture of 1.0-10.0 wt % of ethanol with 0-15.0 wt % of butylene glycol may be used based on the total weight of the skin water.

The emollient may be at least one selected from the group consisting of diethoxyethyl succinate, glyceryl acrylate, acrylic acid copolymer, PEG/PPG-17/6 copolymer, or the like. According to an embodiment, 0-10.0 wt % of diethoxyethyl succinate may be used. According to another embodiment, 0-10.0 wt % of PEG/PPG-17/6 copolymer may be used. According to still another embodiment, a mixture of 0-10.0 wt % of diethoxyethyl succinate with 0-10.0 wt % of PEG/PPG-17/6 copolymer may be used.

The surfactant may be at least one selected from the group consisting of PEG-60 hydrogenated castor oil, octyldodeceth-16, polysorbate 20, octyldodeceth-25, lecithin, caprylyl/capryl glucoside or the like. According to an embodiment, PEG-60 hydrogenated castor oil may be used in an amount of 0.001-1.0 wt %. According to another embodiment, octyldodeceth-16 may be used in an amount of 0-5.0 wt %. According to still another embodiment, a mixture of 0.001-1.0 wt % of PEG-60 hydrogenated castor oil with 0-5.0 wt % of octyldodeceth-16 may be used.

According to an embodiment, the carbonated water may be used in an amount of 0.01-99.0 wt %, particularly 25.0-99.0 wt %, based on the total weight of the skin water. As used herein, the term 'carbonated water' means a solution of carbon dioxide dissolved in water containing suitable salts, and may also be called water containing carbon dioxide. According to an embodiment, it is possible to incorporate at least a predetermined amount of carbonated water to skin water. As a result, carbonic acid bubbles contained in skin water increase the oxygen saturation degree in capillaries and improve the blood circulation, thereby improving the complexion. According to another embodiment, skin barriers are reinforced, differentiation of dead skin cells are facilitated so that old dead skin cells are exfoliated with ease and a healthy corneum is maintained, thereby providing skin whitening, brightening and moisturizing effects. Further, according to an embodiment of the present invention, skin barriers are reinforced, the elasticity around pores is increased and pore shades are removed to provide skin with brightening and pore-care effects.

Hereinafter, construction and preparation of an anhydrous type cosmetic composition of the bubbling tablet according to the present invention will be explained in detail with reference to Examples and Test Examples. However, the present invention is not limited thereto.

EXAMPLE 1 AND COMPARATIVE EXAMPLE 1

Preparation of Bubbling Tablet

Each of the bubbling tablets of Example 1 and Comparative Example 1 is obtained by using the composition as shown in the following Table 1 according to the method as described hereinafter (unit: wt %).

TABLE 1

| Ingredients (wt %)   | Ex. 1 | Comp. Ex. 1 |
|----------------------|-------|-------------|
| Sodium bicarbonate   | 30    | 30          |
| Crystalline citric acid | 15 | —           |
| Powder citric acid   | —     | 15          |
| Mannitol             | 21    | 21          |
| Lactose              | 30    | 30          |
| PVP                  | 1     | 1           |
| Polyethylene glycol  | 3     | 3           |

Preparation of Example 1 and Comparative Example 1

(1) The solid ingredients are mixed homogeneously. However, polyethylene glycol is introduced finally and mixed for about 3 minutes.
(2) The resultant mixture is introduced to a molding machine and pressed into a desired shape, weight and hardness, thereby providing a bubbling tablet.

EXAMPLE 2 AND COMPARATIVE EXAMPLES 2-11

Preparation of Skin Water

Each skin water of Example 2 and Comparative Examples 2-11 is prepared by using the composition as shown in the following Table 2 according to the method described hereinafter (unit: wt %).

TABLE 2

| No. | Ingredients | Ex. 2 | Comp. Ex. 2 | Comp. Ex. 3 | Comp. Ex. 4 | Comp. Ex. 5 | Comp. Ex. 6 | Comp. Ex. 7 | Comp. Ex. 8 | Comp. Ex. 9 | Comp. Ex. 10 | Comp. Ex. 11 |
|---|---|---|---|---|---|---|---|---|---|---|---|---|
| 1 | Water (carbonated water) | 50.00 | 50.00 | 50.00 | 50.00 | 50.00 | 50.00 | 50.00 | 50.00 | 0.001 | 50.00 | 50.00 |
| 2 | Water | To 100 | To 100 | To 100 | To 100 | To 100 | To 100 | To 100 | To 100 | To 100 | To 100 | To 100 |
| 3 | Disodium EDTA | 0.01 | 0.01 | 0.01 | 0.01 | 0.01 | 0.01 | 0.01 | 0.01 | 0.01 | 0.01 | 0.01 |
| 4 | Butylene glycol | 2.50 | 2.50 | 2.50 | 0.01 | 16.0 | 2.50 | 2.50 | 2.50 | 2.50 | 2.50 | 2.50 |
| 5 | Alcohol | 3.00 | 0.50 | 11.00 | 3.00 | 3.00 | 3.00 | 3.00 | 3.00 | 3.00 | 3.00 | 3.00 |
| 6 | PEG-60 hydrogenated castor oil | 0.05 | 0.05 | 0.05 | 0.05 | 0.05 | 0.0001 | 1.10 | 0.05 | 0.05 | 0.05 | 0.05 |
| 7 | Octyldodeceth-16 | 0.10 | 0.10 | 0.10 | 0.10 | 0.10 | 0.10 | 0.10 | 5.10 | 0.10 | 0.10 | 0.10 |
| 8 | Preservative | qsad | qsad | qsad | qsad | qsad | qsad | qsad | qsad | qsad | qsad | qsad |
| 9 | Diethoxyethyl succinate | 0.10 | 0.10 | 0.10 | 0.10 | 0.10 | 0.10 | 0.10 | 0.10 | 0.10 | 11.0 | 0.10 |
| 10 | PEG/PPG-17/6 copolymer | 0.10 | 0.10 | 0.10 | 0.10 | 0.10 | 0.10 | 0.10 | 0.10 | 0.10 | 0.10 | 11.0 |
| 11 | Fragrance | qsad | qsad | qsad | qsad | qsad | qsad | qsad | qsad | qsad | qsad | qsad |

Preparation of Example 2 and Comparative Examples 2-11

(1) Ingredients 1-4 of Table 2 are dissolved to provide an aqueous part.
(2) In a separate container, Ingredients 5-11 of Table 2 are dissolved to provide an alcohol part.
(3) The alcohol part of step (2) is added to the aqueous part of step (1), and the mixture is agitated and solubilized by a mixer to obtain skin water.

TEST EXAMPLE 1

The tablets obtained from Example 1 and Comparative Example 1 are introduced to skin water and the floating behavior of tablet is observed. Example 1 and Comparative Example 1 are provided in the form of a cylindrical type tablet and introduced to 120 ml of skin water to carry out observation. The results are shown in the following Table 3.

TABLE 3

| Bubbling tablets | Ex. 1 | | | | | | |
|---|---|---|---|---|---|---|---|
| Skin water | Ex. 2 | Comp. Ex. 2 | Comp. Ex. 3 | Comp. Ex. 4 | Comp. Ex. 5 | Comp. Ex. 6 | Comp. Ex. 7 |
| Floating time | Floating after 2 min. | Floating within 2 min. | Floating after 2 min. | Floating after 2 min. | Floating after 2 min. | Floating within 2 min. | Floating after 2 min. | Immediately floating |
| Bubbling time | Bubbling for less than 4 min. | Bubbling for less than 4 min. | Bubbling for 4 min. or more | Bubbling for less than 4 min. | Bubbling for 4 min. or more | Bubbling for less than 4 min. | Bubbling for 4 min. or more |
| Reference | | | Dazzling, dryness | Poor moisturizing feel | | Freezing, cold temperature stability turbidity increase | sticky |

| Bubbling tablets | Ex. 1 | | | | Comp. Ex. 1 Ex. 2, Comp. Ex. 2~11 |
|---|---|---|---|---|---|
| Skin water | Comp. Ex. 8 | Comp. Ex. 9 | Comp. Ex. 10 | Comp. Ex. 11 | |
| Floating time | Floating within 2 min. | Floating after 2 min. | Floating after 2 min. | Floating within 2 min. | Immediately floating |

TABLE 3-continued

| Bubbling time | Bubbling for less than 4 min. | Bubbling for less than 4 min. | Bubbling for less than 4 min. | Bubbling for 4 min. or more | Bubbling for 6 min. or more |
|---|---|---|---|---|---|
| Reference | sticky | Carbonated water effect not expected | Turbid content | | |

As shown in Table 3, the combination of Example 1 with Example 2 shows a delay in floating and provides a short bubbling time and excellent bubbling capability. In the other combinations, floating occurs in the early time of bubbling, a long bubbling time is required, or the quality of effect, stability and feel in use are degraded.

TEST EXAMPLE 2

To the same amount of lotion (120 ml of skin water) as Example 2, each of Example 1 and Comparative Example 1 is introduced in the form of a 0.3 g tablet and dissolved completely to provide a solution. After removing the cover of the solution, the solution is allowed to stand at 25° C. for 5 minutes and 0.5 g of calcium hydroxide is added thereto to cause precipitation of calcium carbonate. Then, the precipitate is filtered off and dried to remove water. The dry weight of precipitate is measured. The results are shown in the following Table 4.

TABLE 4

| Item | Ex. 1 | Comp. Ex. 1 |
|---|---|---|
| Amount of dry calcium carbonate (g) | 0.3 g | 0 g |

As the amount of carbon dioxide in lotion increases, the weight of precipitate of calcium carbonate produced through the reaction with calcium hydroxide increases.

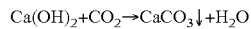

$Ca(OH)_2 + CO_2 \rightarrow CaCO_3\downarrow + H_2O$

As can be seen from the results of Table 4, Example 1 does not float in skin water but forms precipitate to discharge carbonic acid, resulting in a larger amount of calcium carbonate precipitate as compared to Comparative Example 1. Therefore, it can be seen that Example 1 has a larger amount of carbonic acid dissolved in lotion as compared to Comparative Example 1.

TEST EXAMPLE 3

To determine whether skin water provides a different visual effect and brightening effect in use or not, 30 subjects are allowed to participate in the quality test. The results are shown in the following Table 5. Example 1 and Comparative Example 1 are provided in the form of a cylindrical tablet having a weight of 0.3 g. Then, 0.3 g (on the basis of mass) of Example 1 is introduced to 120 ml of the lotion of Example 2. In addition, 0.3 g (on the basis of mass) of Comparative Example 1 is introduced to 120 ml of Comparative Example 9. Then, a survey is conducted by relative evaluation.

TABLE 5

| Item | Ex. 1, Ex. 2 | Comp. Ex. 1, Comp. Ex. 9 |
|---|---|---|
| Different visual effect | Yes, 30 subjects | No, 0 subject |
| Brightening effect after use | Yes 20 subjects, Slight 3 subjects | Not recognized 7 subjects |

As can be seen from Table 5, when the tablet of Example 1 is introduced to the lotion of Example 2, 100% of the subjects recognize a different visual effect and 92% of the subjects recognize a brightening effect after use. This suggests that the combination of a bubbling carbonic acid tablet with lotion provides a different visual effect and brightening effect after use.

As described above, according to an aspect of the present invention, sodium bicarbonate, alpha-hydroxyl acid and crystalline hydroxyl acid are used to form a bubbling tablet. In addition, the composition of an aliphatic compound having a hydroxyl group (—OH), emollient and surfactant in skin water is adjusted to optimize the specific gravity and surface tension. In this manner, it is possible for the bubbling tablet to provide a delay in floating while maintaining excellent bubbling capability in skin water. In addition, according to an embodiment of the present invention, it is possible to incorporate at least a predetermined amount of carbonated water to skin water, as well as to increase the concentration of carbonic acid in skin water during the bubbling of a bubbling tablet. As a result, according to an embodiment of the present invention, on one hand, carbonic acid bubbles contained in skin water increase the oxygen saturation degree in capillaries and improve the blood circulation, thereby improving the complexion. According to an embodiment of the present invention, on the other hand, skin barriers are reinforced, differentiation of dead skin cells are facilitated so that old dead skin cells are exfoliated with ease and a healthy corneum is maintained, thereby providing skin whitening, brightening and moisturizing effects. Further, according to an embodiment of the present invention, skin barriers are reinforced, the elasticity around pores is increased and pore shades are removed to provide skin with brightening and pore-care effects. The cosmetic composition may be applied to various types of cosmetics such as cosmetic toner, mist, essence, mask packs or the like.

Hereinafter, some formulation examples of the cosmetic composition will be explained for illustrative purposes only, and the present invention is not limited thereto.

FORMULATION EXAMPLE 1

Skin Lotion

Skin lotion is prepared according to the composition as shown in the following Table 6 by the conventional method.

TABLE 6

| Ingredients | Amount (wt %) |
| --- | --- |
| Active ingredient containing bubbling tablet and skin water | 0.2 |
| Glycerin | 3.0 |
| Butylene glycol | 2.0 |
| Propylene glycol | 2.0 |
| Carboxyvinyl polymer | 0.1 |
| PEG-12 nonyl phenyl ether | 0.2 |
| Polysorbate 80 | 0.4 |
| Ethanol | 10.0 |
| Triethanolamine | 0.1 |
| Preservative, Pigment, Fragrance | qsad |
| Purified water | balance |

FORMULATION EXAMPLE 2

Milk Lotion

Milk lotion is prepared according to the composition as shown in the following Table 7 by the conventional method.

TABLE 7

| Ingredients | Amount (wt %) |
| --- | --- |
| Active ingredient containing bubbling tablet and skin water | 1.0 |
| Glycerin | 3.0 |
| Butylene glycol | 3.0 |
| Propylene glycol | 3.0 |
| Carboxyvinyl polymer | 0.1 |
| Bees wax | 4.0 |
| Polysorbate 60 | 1.5 |
| Caprylic/capric triglyceride | 5.0 |
| Squalane | 5.0 |
| Sorbitan sesquioleate | 1.5 |
| Liquid paraffin | 0.5 |
| Cetearyl alcohol | 1.0 |
| Triethanol amine | 0.2 |
| Preservative, Pigment, Fragrance | qsad |
| Purified water | balance |

FORMULATION EXAMPLE 3

Nourishing Cream

Nourishing cream is prepared according to the composition as shown in the following Table 8 by the conventional method.

TABLE 8

| Ingredients | Amount (wt %) |
| --- | --- |
| Active ingredient containing bubbling tablet and skin water | 2.0 |
| Glycerin | 3.0 |
| Butylene glycol | 3.0 |
| Liquid paraffin | 7.0 |
| Beta-glucan | 7.0 |
| Carbomer | 0.1 |
| Caprylic/capric triglyceride | 3.0 |
| Squalane | 5.0 |
| Cetearyl glucoside | 1.5 |
| Sorbitan stearate | 0.4 |
| Polysorbate 60 | 1.2 |
| Triethanolamine | 0.1 |
| Preservative, Pigment, Fragrance | qsad |
| Purified water | balance |

FORMULATION EXAMPLE 4

Massage Cream

Massage cream is prepared according to the composition as shown in the following Table 9 by the conventional method.

TABLE 9

| Ingredients | Amount (wt %) |
| --- | --- |
| Active ingredient containing bubbling tablet and skin water | 3.0 |
| Glycerin | 8.0 |
| Butylene glycol | 4.0 |
| Liquid paraffin | 45.0 |
| Beta-glucan | 7.0 |
| Carbomer | 0.1 |
| Caprylic/capric triglyceride | 3.0 |
| Bees wax | 4.0 |
| Cetearyl glucoside | 1.5 |
| Sorbitan sesquioleate | 0.9 |
| Vaseline | 3.0 |
| Paraffin | 1.5 |
| Preservative, Pigment, Fragrance | qsad |
| Purified water | balance |

FORMULATION EXAMPLE 5

Pack

Pack is prepared according to the composition as shown in the following Table 10 by the conventional method.

TABLE 10

| Ingredients | Amount (wt %) |
| --- | --- |
| Active ingredient containing bubbling tablet and skin water | 0.2 |
| Glycerin | 4.0 |
| Polyvinyl alcohol | 15.0 |
| Hyaluronic acid extract | 5.0 |
| Beta-glucan | 7.0 |
| Allantoin | 0.1 |
| Nonyl phenyl ether | 0.4 |
| Polysorbate 60 | 1.2 |
| Ethanol preservative | 6.0 |
| Preservative, Pigment, Fragrance | qsad |
| Purified water | balance |

While the exemplary embodiments have been shown and described, it will be understood by those skilled in the art that various changes in form and details may be made thereto without departing from the scope of this disclosure as defined by the appended claims.

The invention claimed is:

1. A cosmetic kit comprising a bubbling tablet and a skin toner, wherein the bubbling tablet comprises sodium bicarbonate, crystalline citric acid, and a water-soluble lubricant, wherein the skin toner comprises an aliphatic compound having a hydroxyl group (—OH), emollient, surfactant, and carbonated water.

2. The cosmetic kit according to claim 1, wherein the weight ratio of sodium bicarbonate: crystalline citric acid: the water-soluble lubricant is 3.0-70.0: 1.0-70.0:1.0-5.0.

3. The cosmetic kit according to claim 1, wherein the weight ratio of the aliphatic compound having a hydroxyl group (—OH):emollient: surfactant:carbonated water is 1-15:0.1-20:0.001-5.0:0.01-99.0.

4. The cosmetic kit according to claim 1, wherein the carbonated water is used in an amount of 25.0-99.0 wt % based on the total weight of the skin toner.

* * * * *